United States Patent [19]
Rokos et al.

[11] 4,085,206
[45] Apr. 18, 1978

[54] COMPOSITION FOR TREATMENT OF INFECTIOUS DISEASES IN ANIMALS

[75] Inventors: Josef Rokos; Zdeněk Kubat; Pavel Prochazka; Vladislav Zalabák, all of Prague, Czechoslovakia; Josef Babička, deceased, late of Prague, Czechoslovakia, by Marie Babičkova, legal representative; Eva Zemanova, heir; Luboš Babička, heir; Jîrî Janeček, Prague, Czechoslovakia; Miroslav Nohynek, Prague, Czechoslovakia; Petr Mison, Prague, Czechoslovakia

[73] Assignee: Ceskoslovenska akademia ved, Prague, Czechoslovakia

[21] Appl. No.: 659,740

[22] Filed: Feb. 20, 1976

Related U.S. Application Data

[63] Continuation-in-part of Ser. No. 474,247, May 29, 1974, abandoned.

[30] Foreign Application Priority Data

May 31, 1973 Czechoslovakia ................. 3944/73

[51] Int. Cl.$^2$ ............................................. A61K 33/24
[52] U.S. Cl. .................................................. 424/131
[58] Field of Search ........................................ 424/131

[56] References Cited
PUBLICATIONS

Chemical Abstracts 45:4304d (1951).
Chemical Abstracts 54:13434e (1960).
Chemical Abstracts 54:25257i (1960).
The Merck Veterinary Manual, 3rd ed., Merck & Co., Inc., Rahway, N.J. 1967, p. 1403.

Primary Examiner—Jerome D. Goldberg

[57] ABSTRACT

The invention concerns a composition for the treatment and a method of treatment of infectious diseases in animals, e.g. trichophytosis of cattle, orf and cow pox. The active component of the composition contains cobalt chloride at effective concentrations from $10^{-5}$ to $2.10^{-1}$M, prepared in drug form with pharmaceutical carriers.

3 Claims, No Drawings

COMPOSITION FOR TREATMENT OF INFECTIOUS DISEASES IN ANIMALS

This is a continuation-in-part application of our co-pending application Ser. No. 474,247 filed on May 29, 1974 now abandoned.

The invention concerns a composition for curing infectious, particularly viral, diseases in animals. During recent years a number of chemotherapeutic and antibiotic preparations for curing infectious animal diseases have been developed. Nevertheless, there exists a series of etiological agents, such as viruses and related pathogens, in particular, which cause diseases that cannot be causally treated by existing preparations.

The effective component of this invention, i.e., cobalt chloride, may be prepared in the liquid form, suitably as a dispersion, or in a semisolid form, suitably as ointment or gel. The most common forms include solutions of the active component in the form of drops, or solutions for application, rinses or any form of spray. Present chemotherapy makes possible a large number of application forms of active compounds. The composition can be used in all forms of application. However, the most suitable application form with respect to a disease and the concentration or dose of the compound useful for the effective therapy must be selected. The applied dose should be active but non-toxic. Thus, solid and liquid phases, both in aqueous and nonaqueous media and all their combinations can be used for the preparation of different application forms.

According to available knowledge the mechanism of action of $CoCl_2$ on the synthesis of macromolecules in Escherichia coli is primarily based on the synthesis of ribosomes (Blunden, M. R., Bioch. J. 115: 207, 1969).

It was found when studying the effect of different compounds of the Rous sarcoma virus that $Co^{2+}$ inhibits the activity of RNA-dependent DNA polymerase (Levinson et al, Proc. Nat. Acad. Sci USA 70: 164, 1973). This enzyme is present only in a very specific group of oncogenic viruses. Consequently, the effectivity of Co against infections caused by DNA could not be assumed on the basis of the observed inhibition of the activity of RNA-dependent DNA polymerase. Examples presented below demonstrate the effect of active compounds of the composition according to the invention both in experiments in vitro and in experiments with animals and in veterinary medicine.

The first part of the experiments was performed to verify the mechanism of action of the compounds that are the subject of the invention in some bacteria in vitro, $CoCl_2$ being chosen as a typical representative (Examples 1-2). The described composition can be used in all application forms. Therefore, only the most common forms are presented in the Examples. Further examples include toxicity tests in the eye (Examples 3 and 4) and a clinical application of the preparations in veterinary medicine (Examples 5, 6 and 7).

EXAMPLE 1

The effect of $CoCl_2$ on the growth and formation of carboxylic ester hydrolase (E.C.3.1.1. international classification of enzymes according to Enzymes, 2nd Edition, 1964, Malcolm Dixon and Edwin C. Webb) in Mycobacterium phlei and Mycobacteriumsegmatis SN2 (Collection of microorganisms, Borstel, West Germany).

The effect of different concentrations of $CoCl_2$ ($10^{-5}$ to $10^{-9}$M) added to a Sauton nutrient medium (The Bacteriology of Tuberculosis, by Egons Darzins, University of Minnesota Press, Minneapolis 1958 p.227), either during the inoculation, or to a 48-h submerged culture of the bacterial strains was followed in this example. In both examples, growth of microorganisms and changes of the specific activity of carboxylic ester hydrolases of these strains were observed. It was found that $CoCl_2$ added at the beginning of fermentation considerably influenced both the growth and the specific activity of carboxylic ester hydrolase of the studied culture. $CoCl_2$ added to the culture after 48-h of fermentation also considerably influenced the growth of microorganisms. The synthesis of carboxylic ester hydrolase was influenced much more, as shown by the sharp decrease of the specific activity of the enzyme. The fact that the synthesis of carboxylic ester hydrolase was actually inhibited was supported by the finding that the activity of the isolated enzyme was not influenced even at higher concentrations of $CoCl_2$ (e.g., up to $10^{-3}$M).

EXAMPLE 2

The effect of $CoCl_2$ on growth of Escherichia coli, synthesis of beta-galactosidase (E.C.3.2.1.23) and activity of DNA-dependent RNA polymerase.

$CoCl_2$ inhibits completely growth in a synthetic medium during submerged cultivation at concentrations up to $1.10^{-4}$M. Concentrations lower than $1.10^{-5}$M have no effect on growth. It was found by separating the individual steps of the synthesis of inducible beta-galactosidase (Kepes A., Bequin S., Biochim.Biophys. Acta 123: 546, 1966) that $CoCl_2$ inhibits the so-called "enzyme-forming capacity" leading to the assumption that synthesis of a specific messenger RNA is primarily inhibited.

This finding was further confirmed by means of the method of the so-called "elementary wave" (Kepes A., Biochim. Biophys.Acata: 76, 283, 1963). The results show that $CoCl_2$ inhibits the synthesis of messenger RNA.

EXAMPLE 3

Toxicity of $CoCl_2$ on external application

1. Undamaged Tissue

Eye ointments containing 0.5, 2.0 and 5% (W/W) $CoCl_2.6H_2O$ were used to study the toxicity of Co $Cl_2$ in an undamaged epithelium of the eye. The ointment was applied three times per day (8th, 12th and 16th hour) by a glass rod into the conjunctival sac and the extent of damage was evaluated daily, prior to the third application. The evaluation was carried out after staining the epithelium with rose bengale (duodoesin) indicating damage to the cell, accompanied by a pathological permeability of the cell wall to the dye. Even a very weak reaction, such as a thin spotlike dissemination expressed in percent of area of the cornea on which the dissemination was present, was considered as positive. Values presented in the table represent always the average values from five experimental objects. The reaction was more pronounced in a few cases and the spots fused to small facets (about 1 mm²). The number of these cases is designated by crosses in the table.

TABLE 1

Toxicity of CoCl₂ for undamaged surface of the cornea

| $CoCl_2 \cdot 6H_2O$ in % (w/w) $CoCl_2 \cdot 6H_2O$ in ointment | M | \multicolumn{5}{c}{Non-influenced area of the surface of cornea (%)} | | | | |
|---|---|---|---|---|---|---|
| | | 0h | 24h | 48h | 72h | 96h |
| 0.5 | $2.1 \cdot 10^{-2}$ | 100 | 100 | 92 | 97 | 90 ± |
| 2.0 | $8.4 \cdot 10^{-2}$ | 100 | 100 | 95 | 98 | 88 + |
| 5.0 | $2.1 \cdot 10^{-1}$ | 100 | 100 | 90 | 95 | 40 ++ |

EXAMPLE 4

Toxicity of CoCl₂ on external application

2. Damaged Tissue

The toxic effect of CoCl₂ on the division of healthy cells in vivo was studied in a healthy rabbit eye. A ring abrasion (6mm in diameter) was made in the center of the cornea and regeneration of the epithelium was followed. Superimposition of the epithelial effect was evaluated daily after staining with fluorescein. Each of six experimental groups included five animals. The first group was a control without any treatment. Ophthalmo-framycoin (Spofa)-ointment was applied daily to another group and the remaining groups were treated three times a day with eye drops containing $10^{-4}$M, $10^{-3}$M, $10^{-2}$M and $10^{-1}$M CoCl₂. The table shows proportion of regenerated epithelium as related with the area of the original abrasion. The values are mean values always from five experimental objects.

TABLE 2

Toxicity of CoCl₂ in the regeneration of corneal epithelium

| Experimental group | Regenerated area of abrasion in percent | | | | |
|---|---|---|---|---|---|
| | after 24th hour | after 48th hour | after 72nd hour | after 96th hour | after 120th hour |
| Control | 4 | 96 | 100 | | |
| Framycoin (Spofa) | 3 | 83 | 100 | | |
| $10^{-4}$M CoCl₂ | 14 | 85 | 100 | | |
| $10^{-3}$M CoCl₂ | 4 | 80 | 100 | | |
| $10^{-2}$M CoCl₂ | 2 | 81 | 97 | 100 | |
| $10^{-1}$M CoCl₂ | 0 | 0 | 9 | 18 | 50 |

EXAMPLE 5

Local Treatment of Trichophytosis of Cattle

The disease occurs within one or two weeks of placing cattle in a fattening station. Changes are first observed in the vicinity of the eyes, ears and on the neck, the changes being characterized by a pronounced edema and conjunctivitis. Locally demarcated nodules that can be detected only by a careful palpation occur in these predilection sites. They are localized in the skin and the cornified outer layers of the skin including hairs do not exhibit any clinical changes during this phase. Only during further progress of the disease can inflammatory changes associated with an intense proliferation of the stratum corneum infiltrated by an exudate be observed. The clinical picture is a dried pustule. Typical round foci, covered with gray scabs resembling asbestos and attached firmly to the skin are formed after two to three weeks. Their size varies from 0.5 to 5 cm and their depth ranges from 0.5 to 1 cm. They are gradually formed on the head, neck, shoulder blades, loins and other body parts. Cattle from a fattening station, in which trichophytosis in a manifest form was found in bulls, was chosen for a clinical examination.

Five bulls were examined in the first series and a solution containing $10^{-2}$M CoCl₂·6H₂O was used for their local treatment; the second series included also five bulls treated locally with an ointment containing 2% CoCl₂·6H₂O. All bulls were six months old. After transfer to the stable, a disorder characterized by skin changes was observed in 10 days.

Diagnosis: Trichophytosis of cattle, foci localized on the head, around the eyes, ears and neck. Bilateral pronounced edema of the eyelids.

Course of treatment: First day, 9 a.m., a local treatment of the foci around the right eye was performed by attaching gauze wetted in the solution. Exposure time was 5 min. After the application, treated foci and eye conjunctivas turned pink, this color disappearing after 1 hour. No other clinical signs of impairment of the general state of health could be detected. First day, 5 p.m.: It was found by clinical examination that the edema of the lids disappeared on the right side (lids on the left eye are still edematous and swollen). The conjunctiva was pale, asbestos-like crusts able to be removed from the treated foci. Their base did not exhibit signs of inflammation, was round and visibly demarcated, only slightly protruding above the surroundings and evenly covered with short fur. The skin in the neighborhood of the foci was rough. A second local treatment was performed in the same way. Second day, 10 a.m.: Conjunctiva and the eyes did not exhibit any clinical signs of disease, residues of the crusts peeled off. The skin under them was slightly pink and evenly covered with fine fur. The focus on the forehead was freed of the crust after a single treatment, the base having been found to be pale and sharply demarcated.

Third day, 10 a.m.: The crusts were removed from all the treated places, the base was evenly covered with a short fur, without signs of inflammation.

The preparation in the form of a solution was repeatedly used in five other animals and the same results were obtained. In the second group, the following course of healing was followed: First day, 9 a.m.: Foci in the vicinity of the left eye were locally treated by rubbing the ointment into the foci. After the application, the conjunctiva turned slightly pink and vigorous lachrymation for 10 minutes was observed in one case. No general changes of the state of health could be detected. First day, 5 p.m.: The edema retreated, the conjunctiva was pale, the trichophytic crusts readily peeled off, the skin on and in the vicinity of the focus was softened, yet thickened and painless. The base of the foci after the destruction showed no signs of inflammation. It was round, sharply demarcated, slightly protruding above the surrounding area and evenly covered with short fur. Its color was pink. Second day, 10 p.m.: The conjunctiva and the eye showed no signs of the disease. The treated foci were without crusts and occasional residues were readily removed. Third day, 10 a.m.: Crusts were absent from all treated areas. The base showed no signs of inflammation, being evenly covered with short fur.

The preparation in the form of ointment containing 2% CoCl₂·6H₂O was used repeatedly in the other four animals and similar results were obtained. The results of the treatment obtained during the first three days were evaluated as very good.

EXAMPLE 6

Cow Pox (*Variola vaccinia*)

The preparation in question containing 2% $CoCl_2.6H_2O$ (w/w) was applied to 20 cows with typical efflorescences on the udder, mainly on teats and with a considerable inflammation in some of them. The preparation was applied in the form of an ointment once a day. The udder and teats were previously washed. The treatment lasted for 4 days. As compared with other methods of treatment of cow pox, the use of the preparation in the above form appeared more effective and reduced the time of healing by approximately 4–5 days.

EXAMPLE 7

Orf Pustular Dermatitis, Contagious Ecthyma

This viral disease attacks in a high percentage the flocks of sheep and goats. It is manifested by wart-like protrusions or crustae on the mouth, nose and mucosa of the gum and palate of the sick animals. As in the previous example, the preparation was applied in ointment form in 20 lambs only once. As compared with the known method of treatment, the use of the preparation in ointment form appeared very satisfactory and a complete healing was observed 48 hours after application.

Although the invention herein is described with reference to a plurality of exemplary embodiments, it is to be understood that is in no way to be construed as limiting, but rather is capable of numerous modifications within the scope and spirit of the appended claims.

What is claimed is:

1. A method for treating trichophytosis of cattle, orf in sheep and goats or cow pox which comprises topically applying to said animal in need of said treatment a composition comprising from $10^{-5}$ M to $2.1 \cdot 10^{-1}$ M $CoCl_2$ with a pharmaceutical carrier, the composition being employed in an amount sufficient to cure the trichophytosis of cattle, orf or cow pox.

2. Method in accordance with claim 1 wherein the composition is in the form of a gel.

3. Method in accordance with claim 1 wherein the composition is in the form of an ointment.

* * * * *